Figure 1:
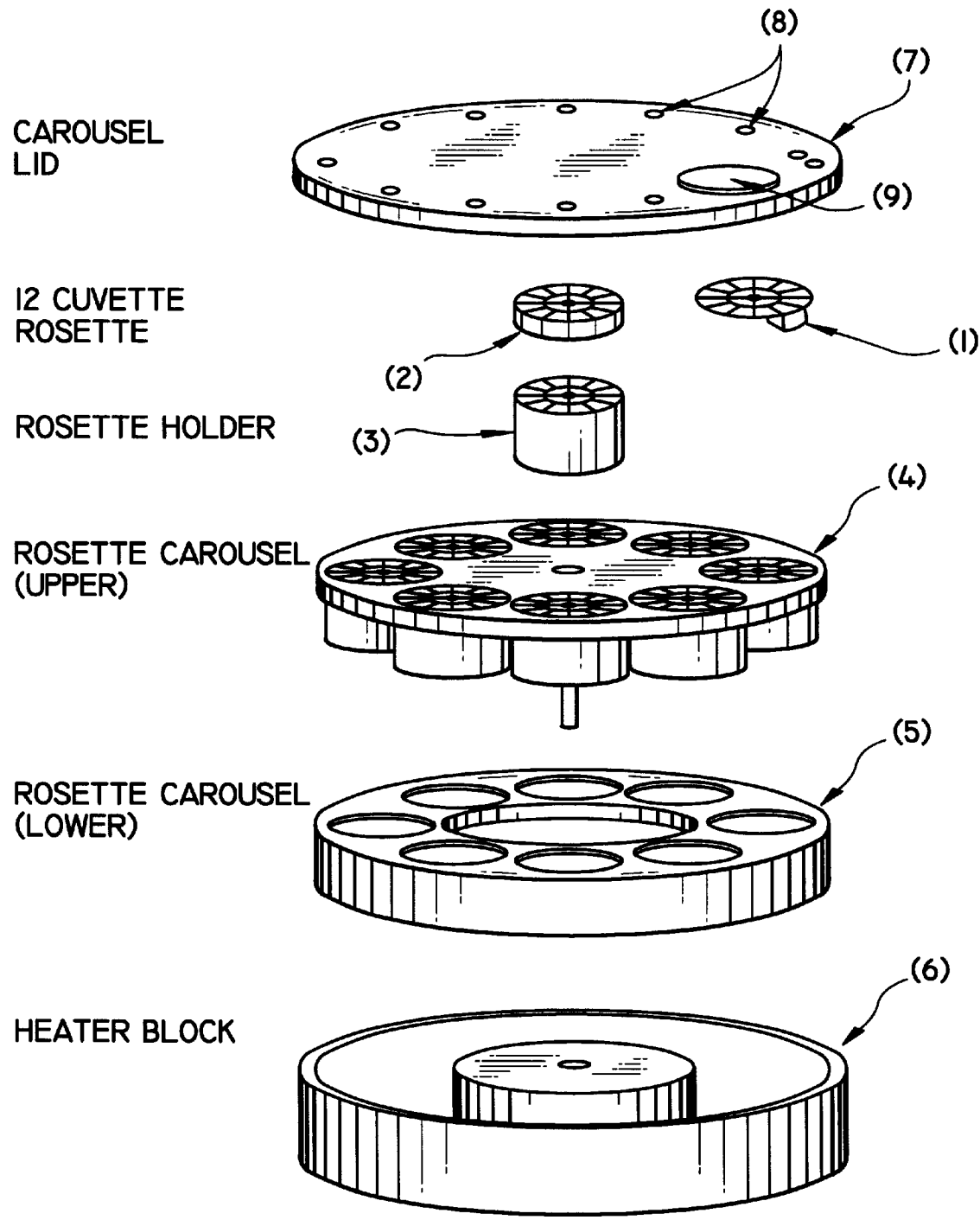

United States Patent [19]
Clements et al.

[11] Patent Number: 6,015,532
[45] Date of Patent: Jan. 18, 2000

[54] INCUBATION VESSEL SUPPORT

[75] Inventors: John A. Clements, Wallington; Ronald F. Jay, Cobham; Paul M. Kemp, Aldershot, all of United Kingdom

[73] Assignee: Alfa Biotech S.p.A., Italy

[21] Appl. No.: 08/776,406

[22] PCT Filed: Jul. 27, 1995

[86] PCT No.: PCT/GB95/01798

§ 371 Date: May 1, 1997

§ 102(e) Date: May 1, 1997

[87] PCT Pub. No.: WO96/03658

PCT Pub. Date: Feb. 8, 1996

[30] Foreign Application Priority Data

Jul. 28, 1994 [GB] United Kingdom ............ 9415232

[51] Int. Cl.⁷ .................................................. G01N 35/02
[52] U.S. Cl. .................... 422/64; 422/63; 422/67; 422/104; 436/43; 436/47; 435/303.1
[58] Field of Search ..................... 422/63, 64, 104, 422/67; 436/43, 47, 48, 807; 435/298.1, 298.2, 303.1

[56] References Cited

U.S. PATENT DOCUMENTS

| | | |
|---|---|---|
| 3,489,521 | 1/1970 | Buckle et al. . |
| 3,623,844 | 11/1971 | Anthon . |
| 4,045,179 | 8/1977 | Bunce ........................ 422/64 |
| 4,849,176 | 7/1989 | Sakagami ................... 422/64 |
| 5,133,936 | 7/1992 | Umetsu et al. . |
| 5,178,833 | 1/1993 | Covain ........................ 422/64 |
| 5,244,633 | 9/1993 | Jakubowicz et al. . |

FOREIGN PATENT DOCUMENTS

| | | |
|---|---|---|
| 0195893 | 10/1986 | European Pat. Off. . |
| 2190889 | 12/1987 | United Kingdom . |

*Primary Examiner*—Long V. Le
*Attorney, Agent, or Firm*—Robert D. Katz; Cooper & Dunham LLP

[57] ABSTRACT

The invention provides an incubation vessel supporting apparatus, including a moveable support and a plurality of incubation vessel mountings carried by the support and moveable independently relative to the support such that, in use, each of the plurality of vessel mountings is simultaneously independently moveable so that each vessel mounted by the mountings is capable of movement to achieve substantially the same temperature/time integral. Such vessel supports can be used in, for example, an automated assay apparatus.

10 Claims, 2 Drawing Sheets

INCUBATOR/ROSETTE DESIGN

INCUBATOR/ROSETTE DESIGN

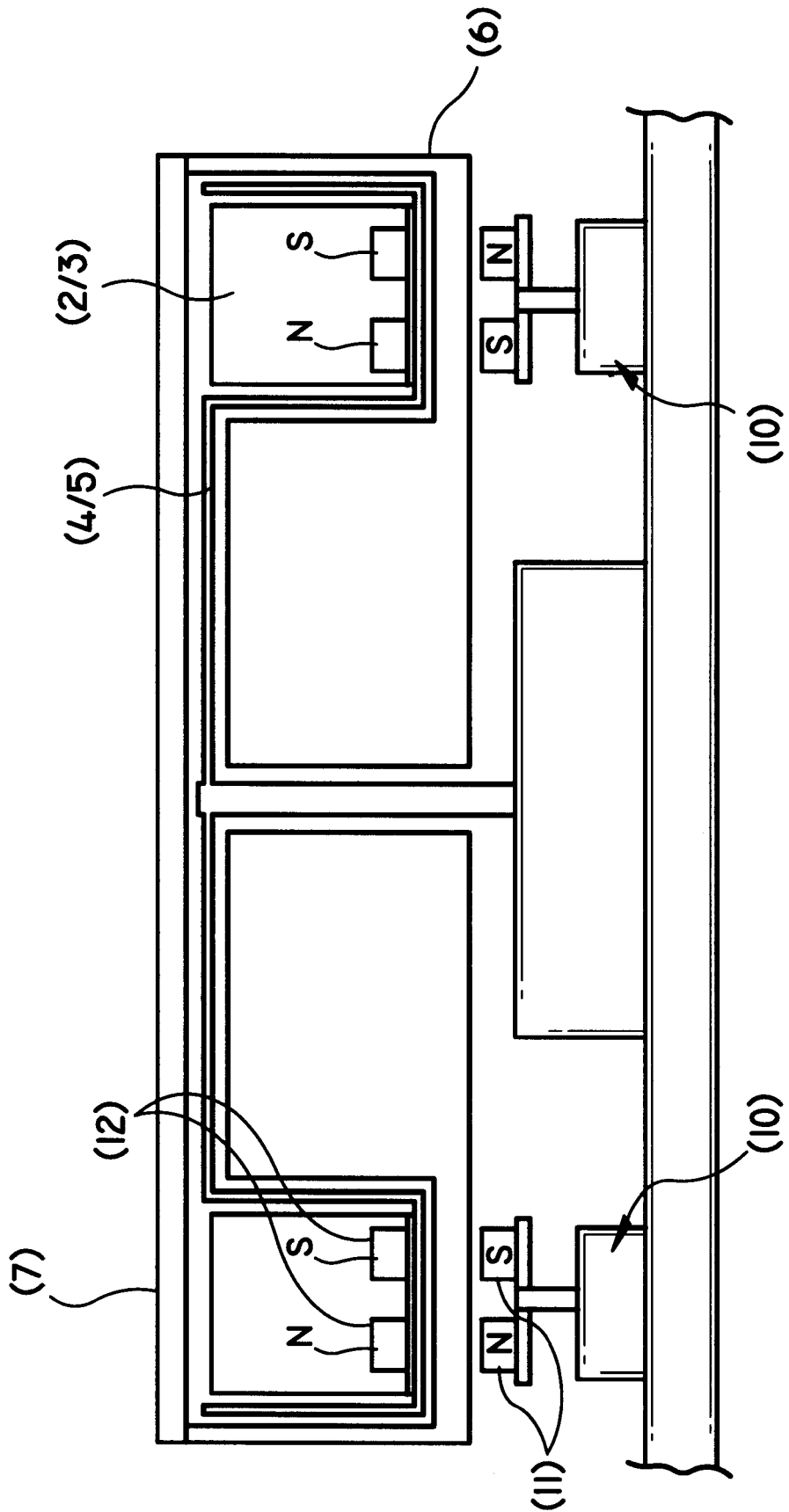

INCUBATION VESSEL SUPPORT

This invention is concerned with incubation vessel supports which enable the effects temperature differences experienced over a period of time by incubation vessels contained within an incubator to be minimized. More particularly, the invention is concerned with incubation vessel supports which are adapted to provide carefully controlled space/time and temperature/time integrals for any particular supported incubation vessel, such integrals being as nearly as possible the same for each such vessel.

Incubators are used in a wide range of applications. Some of those applications dictate careful temperature control, for example biological reactions or carefully controlled chemical reactions. In the area of analysis or testing it can be particularly vital that individual tubes containing samples for testing be subjected to as similar an environment as possible to ensure consistency of results. Immunoassay apparatus in particular demands consistent incubation conditions for individual test.

Lately, complicated apparatus has been developed to permit automation of multiple tests or assays, for example, reference can be made to the apparatus described in WO 92/05448. Unfortunately, there is a problem with such apparatus in that, even in modestly sized incubator chambers, temperature differentials and fluctuations exist across the space within the chamber. With conventional mechanisms for mounting incubation vessels, this means that individual test samples may not necessarily be exposed to sufficiently similar temperature conditions. Even slight variations can have a serious effect on the most precise of assays.

Assay apparatus is known in which incubation vessels are moved between different functional stations, for example, for reagent addition stations to an incubation station (see, for instance, U.S. Pat. No. 5,244,633). In addition, the problem of maintaining temperature control of reaction containers in an automatic analysis apparatus is also known. In U.S. Pat. No. 5,133,936, for example, this is addressed by providing a constant temperature air chamber surrounding a row of reaction containers, the temperature control equipment including an air circulation passage and a blowing device for blowing constant temperature air against the reaction containers. This prior art does not, however, address the specific difficulty of "ironing out" temperature differentials influctuations within incubator chambers as such and the solution to that problem by particularly controlled movement of incubation vessels.

This invention provides an incubation vessel support comprising a moveable platform and incubation vessel mounting means carried by said platform and moveable relative to said platform such that, in use, each vessel mounted thereby is moveable with a space/time integral substantially the same for each said vessel. Because the space/time integral is substantial the same for each vessel, It follows that temperature differences throughout the relevant space are experienced by all such vessels over a period of time, and the temperature/time integral is thus also substantially the same for all such vessels.

The invention is based, inter alia, on the appreciation that an incubation vessel support can be structured in which, over a complete cycle of movement (the word "cycle" not implying any necessity for circularity of movement), any given incubation vessel mounted on the support and within an incubator can be subjected to substantially the same temperature/time integral, even though at any particular point in time individual incubation vessels may be subject to temperature differences.

The concept of the invention will now be further explained and better understood by reference to the following description of an automated analytical system capable of performing chemical analyses, immunoassays or assays involving nucleic acid probes.

In the accompanying drawings:

FIG. 1 shows an incubation vessel support structure in accordance with the present invention, presenting detail shown in exploded form; and FIG. 2 illustrates a preferred drive mechanism for an incubation vessel support structure in accordance with the invention.

Referring first to FIG. 1, the structure of an incubation vessel support in accordance with the present invention can best be appreciated by reference first to carousel upper portion (4). In use, this upper portion is structured to fit within a lower carousel portion (5), and the combination of portions (4) and (5) then fits within a heater block (6). Rosette carousel (4,5) carries (as illustrated) eight reaction cuvette mountings in rosette form (3). The structure of mountings (3) is clearly seen by reference to the upper part of FIG. 1. Each rosette (3) is capable of carrying twelve cuvettes (1). If desired, each rosette (3) may be divided into a number of separable segments to enable most efficient throughput when using long incubation times. In consequence, the overall capacity of the apparatus illustrated is ninety six cuvettes (c.f. standard microtiter plate). Obviously, such numbers are a mere matter of design choice, as the skilled person will appreciate from the general concept described above.

As shown in FIG. 1, each cuvette (1) is segment-shaped. However, this shape is not essential because cuvettes of rectangular or square cross section (or, indeed, any other desired cross section) can be incorporated, as a matter of design choice, around a rosette in a sensibly spaced fashion. Within each rosette mounting (3) a spacing frame work (2) is provided.

Cuvettes (1) are thus positioned within rosette mountings (3), mountings (3) are in turn positioned within carousel (4,5) and carousel (4,5) is within heater block (6). A lid (7) can then be positioned on top of the resulting structure. As shown in FIG. 1, lid (7) has a series of access ports (8) to allow access for pipettes or other aspirators, and one or more (FIG. 1 shows one) larger ports (9) which are covered and allow for individual rosette mountings (3) to be replaced while the incubation vessel support is in use in an incubator.

The function of lower portion (5) is to dissipate heat generated from heater block (6) around rosette mountings (3). However, the skilled reader will appreciate that lower section (5) need not be in solid form as shown in FIG. 1, but could be replaced by heat transfer fluid such as water, or silicone oil, or by gallium metal. Heater block (6) is heated at the bottom and in the centre, and is preferably made of a material ensuring low thermal resistance, for example aluminium or copper.

Lid (7) may, if desired, be heated by a heater mat (not shown) to prevent condensation occurring.

Turning now to FIG. 2, this Figure shows a cross section through an assembled incubation vessel support as shown in FIG. 1, illustrating the mounting of such a support and one means whereby appropriate movement can be achieved. Thus, individual rosette mountings (3) can be rotated at any one of eight carousel stations by the use of eight separate motors (10) mounted underneath heater block (6). [Again, these numbers are, of course, a matter of design choice.] Each motor (10) carries a pair of magnets (11) orientated as shown, which magnets (11) lock onto two appropriately positioned magnets (12) fixed to the bottom of each rosette mounting (3). Thus, when the carousel is rotated such that rosette mountings (3) are positioned at carousel stations above motors (10), magnet pairs (11) and (12) "lock in", and the rosette mountings (3) may be rotated by motors (10).

It will be appreciated that rosette mountings (3) may be rotated clockwise or anti clockwise, whilst the overall rosette carousel (4,5) can be rotated in the opposite or the same direction. By this means, each cuvette (1), is subjected over a complete cycle of rotation to the same space/time integral. Accordingly, the effects of differential temperatures across an incubator (not shown) containing the incubation vessel support of the invention are minimised. Each cuvette (1) is effectively exposed to substantially the same temperature/time integral in the course of its movement through an incubator enclosure. Moreover, the combination of movement of the carousel and of rosette mountings (3) in the manner previously described of course allows any one of individual cuvettes (1) to be brought under an access port (8) in carousel lids (7) for processing.

Although the form of movement described for the apparatus shown in accompanying drawings follows a pattern of circularity, this need not be the case. Thus, and by way of example only, a cuvette holder or support could be structured so as to move backwards and forwards in a reciprocal fashion along a pathway within an incubator container, and with individual cuvette mountings being free to traverse in a direction approximately at right angles to the direction of movement of the carousel. Such a structure could also achieve the same desired effect of equilibration of space/time integral (and hence temperature/time integral) between various cuvettes or incubation vessels held within the incubator. The skilled reader will appreciate that the precise way in which movement is structured is a matter of engineering design and choice within the basic concept of the invention.

In the performance of immunoassays, magnetic particles are frequently used as a solid phase to facilitate separation of material prior to measurement on solid phase or liquid phase. However, other methods of achieving the bound/free separation, such as the use of coated tubes or beads, can also be used within a system employing an incubator according to this invention. The particular apparatus shown in FIGS. 1 and 2 may have a design of each rosette mounting (3) such that magnetisable particles which may be contained within individual cuvettes are not held by magnet pairs (11) or (12) thus preventing resuspension. The upper pair of magnets (12) is bridged by an iron keeper that completes a magnetic circuit between the upper faces of the magnets. Most of the magnetic field will be constrained to pass through this keeper. In addition to this, cuvettes (1) may be separated from this keeper by a distance of 20–30 mm, thus any residual force acting on the particles from magnets (11,12) will be very weak as this force decreases with the square of the distance between the particles and the keeper. The normal distance between the particles and the magnet used to separate them is 2–3 mm. Therefore, the residual force acting on the particles is not large enough to prevent them being readily resuspended by a reversing rotation of rosette mounting (3).

In preferred embodiments of the present invention, an assay apparatus is provided with an incubation vessel support of the invention positioned with a number of work stations arranged around its periphery. Referring particularly to the apparatus shown in FIGS. 1 and 2, for each rosette mounting (3) around carousel (4/5), a work station can be provided. Effectively, since there are eight rosette mountings (3) shown in FIGS. 1 and 2, a work station can be provided for each 45° arc around the circumference of carousel (4/5). Such stations can perform one or more steps of an analysis or complex reaction process, such as pipetting samples or reagents, washing and separating magnetisable solid phase or making measurements on the cuvette contents.

It will be noted that carousel lid (7) as shown in FIG. 1 has two access ports (8) close together at the right-hand side as the lid is positioned in the Figure. This is designed to allow for optical measurement. Thus, one of this pair of ports (8) can be used as an access port for permitting cuvette contents to be transferred to a flow-through cuvette placed in a calorimeter (not shown). The other port (8) at this position/station may be used for a light pipe (not shown) for luminimetric or epifluorimetric measurements.

One considerable advantage of the present invention is its great flexibility and adaptability. The principle described herein can be applied to any automated analytical or reaction system with appropriate routine engineering modification apparent to the skilled reader. The principle of the Invention offers some distinct advantages for incubators In automated analytical systems as compared to incubator structures used in the art. These advantages include, but are not limited to, the following:

1. As already explained above, movement of incubation vessels/cuvettes (1), together with different and separately controlled movement of carousel (4/5), averages out for each vessel/cuvette (1) temperature differences experienced across the interior of an incubator.
2. Work stations can be stationary with only the incubation vessel support moving such that individual incubation vessels/cuvettes (1) are positioned, as required, adjacent work stations. This means that any overall system incorporating an incubation vessel support of the present invention requires a minimum of moving parts, reducing costs and simplifying engineering design.
3. Particularly with structures as illustrated in Figures in 1 and 2, rotational movement of carousel (4/5) in predetermined increments (for example, 45°), and in chosen time intervals, allows cuvettes (1) to be processed at access stations in such a way that the performance of random access analyses may be carried out without seriously reducing single analyte throughput. System operational efficiency is thus maximised.
4. The principle of the invention permits the design of incubation vessel supports which are adapted to hold a considerable number of individual vessels/cuvettes (1), permitting incubation of a large number of such vessels/cuvettes (1) in a relatively small incubator. Moveover, decreasing the size of the surroundings of an incubation vessel support is of itself a contribution towards maintaining correct and uniform temperature control. For example, a carousel as illustrated in FIGS. 1 and 2 could typically have a diameter of the order of 20 to 25 cm, although this is not, of course, in any way limiting upon the present invention.

We claim:

1. An incubation vessel supporting apparatus, comprising a moveable support and a plurality of incubation vessel mountings carried by said support and moveable independently from one another and relative to said support such that, in use, each of said plurality of vessel mountings is simultaneously independently moveable so that each said vessel mounted by said mountings is capable of movement to achieve substantially the same temperature/time integral.

2. A supporting apparatus as claimed in claim 1, wherein said support is rotatable about a central axis.

3. A supporting apparatus as claimed in claim 1, wherein each of said mountings is adapted to contain a plurality of incubation vessels.

4. A supporting apparatus as claimed in claim 1, wherein said mountings are adapted to permit incubation vessel movement in a circular pathway.

5. A supporting apparatus as claimed in claim 4, wherein said mountings comprise one or more rotatable incubation vessel carousels on said platform.

6. An incubator comprising an incubation chamber, chamber temperature control means, and a supporting apparatus as defined in claim 1 positioned in said chamber.

7. An incubator as claimed in claim 6, wherein said temperature control means comprises a heater block adapted to be positioned around said support.

8. An automated assay apparatus incorporating either a supporting apparatus as defined in claim 1 or an incubator as defined in claim 6 with said support being associated with optical measurement means for performing optical measurements upon the contents of an incubation vessel mounted on said supporting apparatus.

9. An apparatus as claimed in claim 8 and also comprising a plurality of work stations positioned around the periphery of said support such that, in use, an incubation vessel mounted on said supporting apparatus may be moved between work stations by movement of said support.

10. An incubation vessel supporting apparatus as claimed in claim 2, wherein each said vessel mounting is rotatable about said axis of said moveable support and about an axis of said mounting simultaneously with each other mounting.

* * * * *